United States Patent [19]

Rosman et al.

[11] Patent Number: 5,079,170
[45] Date of Patent: Jan. 7, 1992

[54] METHOD OF SAMPLE TRANSFER USING A FILTER APPLICATOR

[75] Inventors: Daniel B. Rosman, Mountain View; Douglas D. Rundle, Menlo Park; Gary A. Ascani, Redwood Shores; Richard B. Mortensen, Menlo Park; Henry Tom, La Honda, all of Calif.

[73] Assignee: Quidel Corporation, San Diego, Calif.

[21] Appl. No.: 604,398

[22] Filed: Oct. 25, 1990

Related U.S. Application Data

[63] Continuation of Ser. No. 353,841, May 18, 1989, abandoned, which is a continuation-in-part of Ser. No. 128,260, Dec. 3, 1987, abandoned.

[51] Int. Cl.⁵ .................. G01N 33/16; G01N 33/551; A61K 43/00; B01L 3/02
[52] U.S. Cl. .................. 436/178; 422/58; 422/100; 422/101; 436/177; 436/180; 210/767; 210/504; 210/505
[58] Field of Search ........... 422/58, 64, 70, 81, 422/100, 101, 102; 436/177, 178–180, 527; 210/399, 504, 505, 508, 509, 767, 782

[56] References Cited

U.S. PATENT DOCUMENTS

| | | | |
|---|---|---|---|
| 2,509,872 | 5/1970 | Truhan | 422/58 |
| 3,873,682 | 3/1975 | Ogawa | |
| 3,985,032 | 10/1976 | Avakian | 73/425.4 |
| 4,087,248 | 5/1978 | Miles | |
| 4,138,474 | 2/1979 | Updike | 422/58 |
| 4,151,254 | 4/1979 | Gimovsky | 422/71 |
| 4,155,711 | 5/1979 | Zelagin et al. | 422/71 |
| 4,291,904 | 7/1983 | Litman et al. | |
| 4,393,141 | 7/1983 | Schueter et al. | 422/101 |
| 4,477,578 | 10/1984 | Miles et al. | |
| 4,483,825 | 11/1984 | Fatches | |
| 4,487,696 | 12/1984 | Ferrara | |
| 4,635,488 | 1/1987 | Kremer | 422/58 |
| 4,734,262 | 3/1988 | Bagshawe | 422/102 |
| 4,747,955 | 5/1988 | Kunin | 210/505 |
| 4,753,775 | 6/1988 | Ebersole et al. | 422/102 |
| 4,775,635 | 10/1988 | Ebersole et al. | 436/527 |
| 4,806,313 | 2/1989 | Ebersole et al. | 422/102 |
| 4,818,677 | 4/1989 | Hay-Kaufman et al. | |
| 4,859,336 | 8/1989 | Savas et al. | 422/101 |
| 4,874,691 | 10/1989 | Chandler | 422/101 |
| 4,876,191 | 10/1989 | Hollander et al. | 435/178 |
| 4,941,808 | 7/1990 | Qureshi et al. | 417/415 |
| 4,978,504 | 12/1990 | Nason | 422/101 |

FOREIGN PATENT DOCUMENTS

| | | |
|---|---|---|
| 0276152 | 7/1988 | European Pat. Off. |
| 0312394 | 4/1989 | European Pat. Off. |
| 0321145 | 6/1989 | European Pat. Off. |
| 3214287 | 12/1982 | Fed. Rep. of Germany ...... 422/102 |
| WO86/00704 | 1/1986 | PCT Int'l Appl. |
| 1341152 | 12/1973 | United Kingdom |

OTHER PUBLICATIONS

Testpack Assay System, Abbott Laboratories, North Chicago, Ill.

Primary Examiner—David L. Lacey
Assistant Examiner—Kimberly A. Trautman
Attorney, Agent, or Firm—Townsend and Townsend

[57] ABSTRACT

A sample applicator for use in performing immunoassays comprises a tube defining an internal lumen and having a filter matrix at one end thereof. Sample is drawn into the applicator tube, either using a vacuum bulb or an automated assay device. The sample is filtered as it enters the tube, and is again filtered as it discharged from the tube in the opposite flow direction. By removing particulates from the liquid sample, assay performance can be greatly improved. The applicator may also comprise a reagent dispersed within a permeable matrix, which is useful for introducing reagent to a sample or other liquid assay component. As a liquid assay component is drawn into the applicator tube, the reagent is reconstituted by and mixed with the liquid, thereby reducing the number of steps required for the assay.

28 Claims, 1 Drawing Sheet

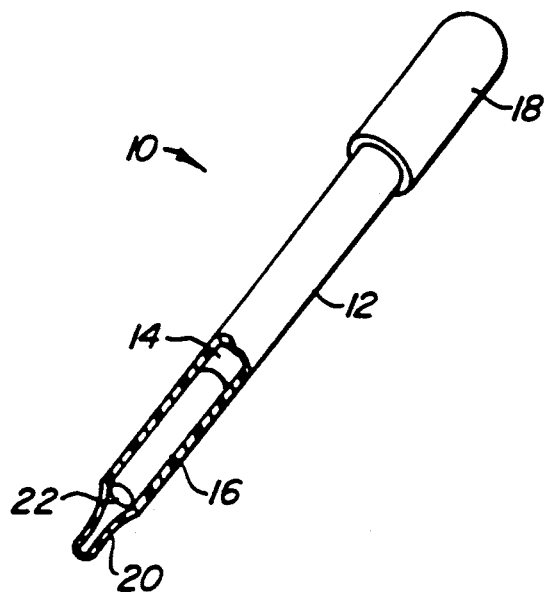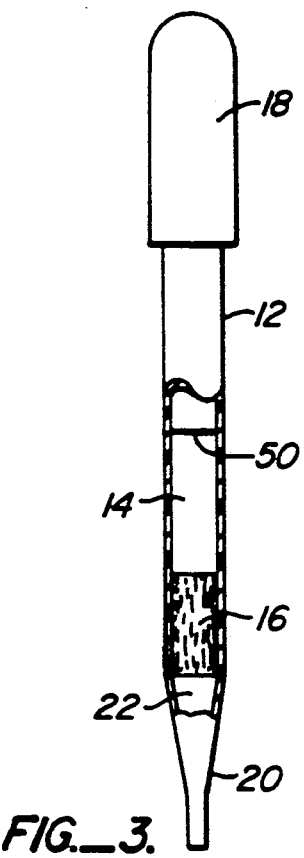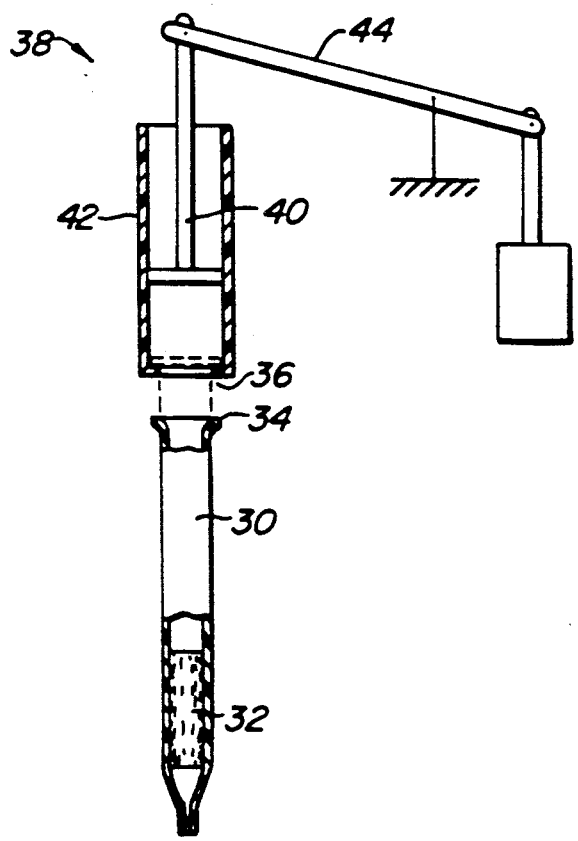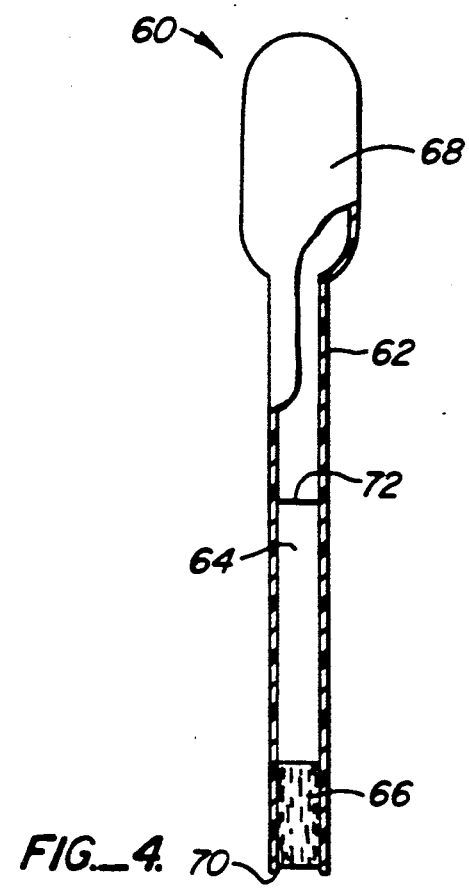
FIG._1.
FIG._3.
FIG._2
FIG._4.

METHOD OF SAMPLE TRANSFER USING A FILTER APPLICATOR

This is a continuation of application Ser. No. 07/353,841, filed May 18, 1989, now abandoned which is a continuation-in-part of application Ser. No. 128,260, filed on Dec. 3, 1987, now abandoned.

BACKGROUND OF THE INVENTION

1. Field of the Invention

The present invention relates generally to methods and apparatus for determining analytes in biological specimens. More particularly, it relates to the construction and use of a liquid sample applicator having an internal matrix which removes particulates from the sample and to a liquid sample applicator having a permeable internal filter with a reagent dispersed therein.

2. Description of the Background Art

The immunoassay of biological specimens has proved to be of enormous benefit in a variety of circumstances, such as the diagnosis of disease, detection of drugs, and monitoring of physiological metabolites. In performing immunoassays on liquid biological samples, pretreatment is frequently required to remove particulates, such as cellular debris, which might foul the assay apparatus or interfere with the assay results. The particulates may be removed, for example, by filtering the liquid sample during a separate step in the assay procedure. Although effective to overcome the interference problems, the addition of a filtering step is undesirable as it adds to the time and complexity of the assay procedure. It would therefore be desirable to provide filtering procedures and apparatus which would be integral to the assay protocol and would not add time or complexity to the overall procedure.

One attempt to simplify the filtering of biological samples undergoing immunoassay procedures is described in U.S. Pat. No. 3,873,682, to Ogawa. A filter cartridge is detachably mounted on the tip of a pipette or fluid dropper. By drawing sample upward through the filter into the pipette, the particulates are removed. The filter is discarded prior to discharging the sample into an appropriate assay media. Although effective in removing particulates, the device of Ogawa is relatively expensive as it consists of two separate pieces. Moreover, the method requires an extra step to discard the cartridge. In addition to extending the time required to perform the assay, the need to discard the filter cartridge would complicate use of the pipette in most automated systems for performing immunoassays. Pipettes manufactured in accordance with the patent are commercially available from Mochida Seiyaka Kabushiki Kaisha, Tokyo, Japan.

Pipettes or dispensers containing an integral filter are disclosed in U.S. Pat. Nos. 4,483,825 (to Fatches) and 4,487,696 (to Ferrara). These patents are directed to the separation of blood cells from plasma in centrifuged blood samples. Each discloses a tube having an inlet end containing a filter through which the plasma is passed. However, the filtered serum is then poured out of the tube through the opposite, or outlet end. While such a method would remove particulates, it would be necessary to remove the bulb from the top of the fluid dropper prior to dispersing the filtered liquid, thus adding an extra step and additional time to the assay process. Additionally, dispersing the fluid from the opposite end of the tube would be unworkable in most if not all automated immunoassay systems and with one-piece pipettes.

A different approach for sample filtration is found in the TestPack® assay system available from Abbott Laboratories, North Chicago, Ill., and the Preview Serum/Urine-hCG assay system available from Leeco Diagnostics, Inc., Southfield, Michigan. In both cases, a detachable filter is snapped into place against a membrane having bound antibodies specific for the analyte of interest. Sample is applied to the membrane through the filter, and the filter removed prior to development of the assay. Although functional in removing particulates, use of such assay systems has certain disadvantages. In particular, the time required for the sample to penetrate the filter can be as long as one minute or more, adding to the time necessary to perform the assay. Moreover, the need to remove the filter holder prior to development is an extra step which further extends the time required to perform the assay and which, if forgotten, can ruin the test results completely.

For these reasons, it would be desirable to provide a method and apparatus for filtering biological specimens during immunoassay procedures, which methods and apparatus do not require any additional steps or procedures, which do not extend the time required to perform the assay, and which still provide the improved assay results associated with the more cumbersome filtering techniques described above.

Additionally, biological assays often require the combination of one or more reagents with a test sample or other liquid assay component during the course of the assay. Heretofore, reagent addition has generally required discrete addition step(s) performed at appropriate times during the assay. While certainly workable, each additional assay step increases the assay complexity, the time required to perform the assays, and the chance that contaminants and errors will be introduced into the final result. It would therefore be desirable to perform reagent combination(s) concurrently with the transfer of liquid sample or other liquid assay component, thus reducing the number of actual assay steps involved, with a concomitant reduction in time and effort required to perform the assay.

SUMMARY OF THE INVENTION

The present invention provides a novel applicator for transferring liquid samples during immunoassay procedures. The applicator includes an integral filter matrix which provides for bi-directional filtering of the sample at any stage of the assay procedure, typically during the transfer of the sample from a reservoir to an assay device or media. That is, the liquid sample will initially be drawn into the applicator in a first flow direction through the filter matrix and thereafter discharged through the filter matrix in the opposite flow direction.

The applicator comprises a tube defining an internal lumen and a filter matrix disposed within the lumen at one end of the tube. By first drawing the liquid sample from the reservoir into the tube and then discharging the sample to the assay device or media, the sample passes through the filter matrix twice. Surprisingly, it has been found that discharge of the sample back through the filter matrix does not result in any substantial release of the particulates or other substances which can interfere with the subsequent performance of the assay. Thus, the immunoassay can be performed with filtering of the sample, but without any additional time or steps required for the assay performance.

In the specific embodiments of the present invention, the applicator may comprise a fluid dropper having a vacuum bulb mounted on the end of the tube opposite the filter matrix. The fluid dropper may then be used in any assay procedure requiring the manual transfer of the sample using a dropper or pipette. Alternatively, the applicator may be used in automated immunoassay machines with a plurality of the applicators mounted on a common vacuum apparatus. Carefully controlled volumes of sample are drawn into the applicators and a plurality of assays performed simultaneously. For use in such automated systems, the applicators of the present invention will usually be modified at their remote ends to allow for detachable mounting on the vacuum apparatus.

Use of the filter applicator of the present invention has proved to be particularly valuable in performing urine assays for human chorionic gonadotropin (hCG) and luteinizing hormone (LH) where interference from various particulate and soluble substances has heretofore been problematic.

The present invention further provides a novel applicator for introducing a reagent to a liquid biological sample or other liquid assay component. The applicator comprises a tube defining an internal lumen and including an integral permeable matrix having a reagent dispersed therein. As a liquid sample or assay component is drawn through the permeable matrix and into the applicator, the reagent component is combined with and released into the sample or other liquid assay component. The sample and reagent are thereafter discharged through the permeable matrix to an assay medium or device. This results in a reduction in the number of steps in the assay since the requirement of measuring out and adding (as by counting drops) of reagent to the sample or other assay component or of sample and/or reagent to the assay medium or device prior to or following transfer of the sample or other assay component is eliminated.

BRIEF DESCRIPTION OF THE DRAWINGS

FIG. 1 illustrates a first embodiment of the applicator of the present invention intended for the manual transfer of liquid samples.

FIG. 2 is a schematic illustration of the use of the applicator of the present invention in an automated immunoassay device.

FIG. 3 illustrates another embodiment of the applicator of the present invention which includes a membrane at a fill line in the applicator tube.

FIG. 4 illustrates a further embodiment of the applicator of the present invention which is a one-piece applicator where the vacuum bulb is an integral part of the applicator and is not removeable.

DESCRIPTION OF THE SPECIFIC EMBODIMENTS

According to the present invention, a liquid sample applicator comprises a tube defining an internal lumen and having a filter matrix disposed within the lumen at one end of the tube. The applicator may further include a vacuum bulb at its other end so that it may be used in a manner similar to the use of a conventional fluid dropper in transferring liquid samples in performing immunoassays. Alternatively, the other end of the applicator may be adapted for mounting on a vacuum apparatus which forms part of an automated assay machine. In that case, the applicator may further include immunological reagents immobilized on its internal surface, and the applicator may be used in otherwise conventional automated assay protocols. In both cases, the inclusion of the filter matrix provides bi-directional filtering of the sample fluid to remove particulates which might otherwise interfere in the assay. Such filtering is achieved without additional assay steps or time required for performance of the assay. Surprisingly, it has been found that discharge of the sample through the filter matrix does not result in any appreciable release of the particulates back into the liquid sample.

The present invention is useful in assaying for a wide variety of soluble analytes in virtually any type of biological sample which is liquid or which can be liquified. The method and apparatus will find its greatest use with specimens, such as blood, serum, plasma, urine, cerebral fluid, spinal fluid, ocular lens liquid (tears), saliva, sputum, semen, cervical mucus, scrapings, swab samples, and the like. Use of the filter applicator of the present invention has proved to be particularly valuable in performing urine assays for human chorionic gonadotropin (hCG) and luteinizing hormone (LH) where interference from various particulate and soluble substances has heretofore been problematic.

The samples will generally include particulate contaminants which can interfere in the assay procedure in some manner. For example, the particulates might chemically interfere with the immunological reactions necessary for analyte detection, might mechanically interfere with the assay procedure, such as by plugging ports or membranes, or might interfere with the determination of assay results, such as by affecting optical density readings. Such interfering particulates may derive from a variety of sources, such as cellular debris, mucus, precipitated biological salts, and the like.

Referring now to FIG. 1, an applicator 10 constructed in accordance with the principles of the present invention includes an elongate tube 12 defining an internal lumen 14 and having a filter matrix 16 disposed within the lumen at one end of the tube. In the first embodiment of FIG. 1, the applicator 10 further includes a vacuum bulb 18 mounted at the end opposite the filter matrix. The bulb 18 is in sealing engagement with the tube 12 so that manipulation of the bulb will cause fluid to be drawn into or expelled from the lumen 14. The tube 12 may be formed from a variety of materials, including glass, metals, ceramics, organic polymers, such as polypropylene, polyvinylchloride, nylon, polyethylene, and the like. The vacuum bulb 18, will typically be formed from an elastomeric polymer, such as natural rubber. Normally, the end 20 of the tube 12 proximate the filter matrix 16 will be tapered. However, this is not required, as is illustrated by end 70 in FIG. 4. Construction of the tube 12 and the vacuum bulb 18 will be similar to that employed for conventional fluid droppers, and commercially available fluid droppers may be used in fabricating the applicators 10 of the present invention.

The filter matrix 16 will be capable of removing particulates having dimensions as small as about 2 $\mu$m, usually as small as about 1 $\mu$m, and preferably as small as about 0.5 $\mu$m and below. The particles, of course, may be much larger, frequently being 3 $\mu$m or greater. At least about 75% of the smallest particulates initially present in the liquid sample will be removed, usually being at least about 90% of such particulates, and more usually being at least about 95% of such particulates. The filters should be formed from a material which is substantially free from binding of the analyte of interest. Frequently, however, it will be desirable for the filter media to remove soluble substances (other than the analyte) including ions, organic molecules, such as creatinines, bilirubins, pigments, and hemoglobin, and inorganic molecules. Suitable materials include polyesters, cellulose acetates, polyacrylonitriles, and the like. Particularly preferred are filter matrices formed from poly(ethylene terephthalate) which is a polyester having the empirical formula $[C_{10}H_8O_4]n$.

In order to obtain efficient particulate removal, it is necessary that the filter matrix 16 be arranged so that the liquid sample will pass through the material rather than merely by the filter material. Thus, certain filter configurations, such as a spiral roll where sample can channel through adjacent layers, are unsuitable. Suitable configurations include placing a filter membrane across the lumen 14 of the applicator 10 so that flow must pass through the membrane, or packing a filter media within the lumen sufficiently tightly so that flow through the media is assured.

The filter matrix 16 is preferably formed from polyester fibers having a diameter in the range from about 5 to 50 μm, usually in the range from about 10 to 20 μm. The fibers will be arranged in a bundle having a plurality of fibers arranged parallel to one another at a sufficient density of about $1 \times 10^5$ to $5 \times 10^5$ fibers/cm$^2$, usually being about $2.5 \times 10^5$ fibers/cm$^2$ for fibers having a diameter of 15 μm. The bundle will usually be mechanically bound, typically in a thin plastic tube, to facilitate handling and insertion into the elongate tube 12. The individual fibers should be free from adhesives and other bonding agents, as adhesives will frequently cause protein binding which will affect the composition of the sample, i.e., will remove analyte therefrom. The length of the fibers will depend on the dimensions of the applicator and the volume of sample to be treated, usually varying in the range from about 0.25 to 5 cm, the fiber bundle will be arranged within the tube so that the fibers lie in the axial direction.

Conveniently, the fiber bundle will be inserted through the open end of tube 12 (which is secured by bulb 18) and pushed forward to the location illustrated in FIG. 1. With applicators having tapered tips 20, small void volume 22 will be left within the tip which will hold non-filtered sample as the assay is being performed. As described in more detail hereinafter, it may be desirable to discard a portion of the sample equal to the volume held in the void volume 22 to provide maximum reduction of the particulates in the sample transferred to the assay device or media.

An alternative applicator construction is illustrated in FIG. 2. Applicator tube 30 is constructed similarly to applicator tube 12 and includes a filter matrix 32. Applicator tube 30, however, does not include a vacuum bulb, and instead terminates with an open flange 34 on the open end opposite the filter matrix 32. The flange 34 may be inserted into a port 36 on a vacuum apparatus 38 which forms part of an automated assay machine. The vacuum apparatus 38 is schematically illustrated to include a syringe plunger 40 mounted in a syringe cylinder 42 with a powered lever 44 for reciprocating the plunger 40 up and down. It will be appreciated that when the tube 30 is in place within port 36, as illustrated in broken line, the syringe plunger will be able to draw fluid up into the tube 30 and expel fluid from the tube in a conventional manner.

The construction of the automated assay system may, of course, vary widely, and it is anticipated that the open end of the tube 30 may be adapted to mate with a wide variety of vacuum apparatus in different automated assay machines. Exemplary automated assay machines are disclosed in U.S. Pat. Nos. 4,087,248 and 4,477,578, the disclosures of which are incorporated herein by reference. A number of other compatible assay systems are available commercially.

When incorporated in an automated assay system, it may be desirable to coat the inside surface of the applicator tube 30, particularly the portion located above the filter matrix 32 with an immunologically active substance, such as antibody, antigen, and the like. The immobilization of such substances within is amply described in the patent and scientific literature. In this way, certain immunological binding step(s) of the assay may be performed concurrently with the sample transfer step(s).

Another alternative applicator construction is illustrated in FIG. 4. Applicator 60 is constructed of one piece, with the vacuum bulb 68 and tube 62 integrally forming the applicator. Bulb 68 is not removeable from tube 62. Tube 62 defines an internal lumen 64 and has a filter matrix 66 disposed within the lumen at one end of the tube opposite the vacuum bulb. The end 70 proximate the filter matrix 66 is normally flat. A fill line 72 may optionally be included in this or other applicators of the present invention to assist in the determination of volume of sample or other assay component to be drawn up into the applicator in the practice of the invention.

When the fiber bundle comprising the filter matrix 66 is inserted into the one-piece applicator 60, it will conveniently be inserted through the open end 70.

The applicators of the present invention may be used in any assay protocol which employs the use of a fluid dropper or which may be performed in an automated assay machine utilizing detachable pipette tips for sample transfer, incubation, reading, or the like. For example, the applicator 10 may be used for transferring liquid sample from a sample reservoir, such as a specimen cup, to an assay medium or device, such as a test tube, microtiter well, assay membrane, or the like. A particular assay protocol employing a membrane assay device wherein the applicator of the present invention may be utilized is described in U.S. Pat. No. 4,818,677, which is incorporated herein by reference.

Generally, the assay device will be capable of immunologically binding the analyte to be detected, and the bound analyte will be visualized on the device, typically by reaction with enzyme-labeled antibody specific for the analyte and exposure to enzyme substrate. Enzyme-substrate systems capable of producing a colored reaction product are amply described in the patent and scientific literature.

Biological assays often require the combination of one or more reagents with the test sample or other liquid assay component during the course of the assay. Heretofore, reagent addition has generally required discrete addition step(s) performed at appropriate times during the assay. While certainly workable, each additional assay step increases the assay complexity, the time required to perform the assays, and the chance that contaminants and errors will be introduced to the final result. It would therefore be desirable to perform reagent combination(s) concurrently with the transfer of liquid sample or other liquid assay component, thus reducing the number of actual assay steps involved, with a concomitant reduction in time and effort required to perform the assay.

Therefore, the present invention further provides a novel applicator for introducing a reagent to a liquid biological sample or other liquid assay component. The applicator includes an integral permeable matrix (usually a filter as described above) having a reagent dispersed therein. As a liquid sample or assay component is drawn through the permeable matrix and into the applicator, the reagent component is combined with and released into the sample or other liquid assay component. The sample and reagent are thereafter discharged through the permeable matrix to an assay medium or device, such as a test tube, microtiter well, assay membrane, or the like. Thus, the number of steps in the assay is reduced since the requirement of measuring out and adding (as by counting drops) of reagent to the sample or other assay component or of sample and/or reagent to the assay medium or device prior to or following transfer of the sample is eliminated.

According to the invention, the applicator for use in introducing a reagent component to a liquid sample or other assay component comprises a tube defining an internal lumen, a permeable matrix disposed within the lumen at one end of the tube, and a reagent dispersed within the permeable matrix. The applicator further includes a means for aspirating sample into the tube and expelling sample from the tube. The means may include a vacuum bulb at the other end of the tube so that it may be used in a manner similar to the use of a conventional fluid dropper in transferring liquid samples or other components in performing assays. Alternatively, the other end of the applicator may be adapted for mounting on a vacuum source which forms part of an automated assay apparatus. Generally, the applicator will be of the general construction as embodied in FIGS. 1, 2, 3 and 4.

The permeable matrix 16, 32 or 66 will be chosen from those materials which can reversibly entrap the reagent but will not irreversibly bind it, while allowing passage of the liquid component, so that as the liquid component passes through the matrix the reagent is released. The permeable matrix will usually be formed from filtering materials as described above, including cellulose acetates, bonded or unbonded polyesters, polyacrylonitriles, nylon, cotton, and any other manmade or natural fiber or porous material which meets (or can be modified to meet) the above criteria. Additionally, the permeable matrix may be formed from a variety of inorganic materials, including ceramics, glasses, silicas, and the like, which may be formed into a porous substrate, typically by sintering. If it is desired for the permeable matrix to also be capable of removing particulates, the permeable matrix must also have this filtering characteristic, as discussed previously herein. In one preferred embodiment, the matrices will be filtering matrices formed from poly(ethylene terephthalate), which is a polyester having the empirical formula [$C_{10}H_8O_4$]n. Other preferred materials include cellulose acetates and polyacrylonitriles.

The volume or mass of the permeable matrix 16 or 32 in the tube 12 or 30 will depend on the physical and/or chemical characteristics of the particular matrix material, the dimensions of the applicator, and the particular reagent to be used and its volume, as well as the volume of sample or other liquid component to be treated. Usually, sufficient permeable matrix material will be provided to promote rapid and uniform transfer of the reagent component into the sample or other liquid. The matrix volume, however, should not be so large that it results in unacceptable hold-up of sample or other liquid in the matrix. The height of the permeable matrix in the exemplary tube embodiment will usually vary in the range from about 0.25 to 5 cm, more usually in the range from about 0.5 to 1.5 cm.

The reagent may be any substance which can react or otherwise interact with the analyte, sample liquid, or other liquid assay component. Such reagents may be chosen from, but are not limited to, salts; buffering salts; free monoclonal or polyclonal antibodies; monoclonal or polyclonal antibody conjugates; free proteins; colloidal suspensions; bead structures; antigens; haptens; cofactors; activators; scavengers; inhibitors; stabilizers; surfactants; and labels, such as enzymes, dyes, fluorescers, chemiluminescers, spin labels, radionuclides, biotin, avidin and the like. Such reagents and their use are amply described in the patent and scientific literature. A comprehensive list of some of the possible reagents is presented in U.S. Pat. No. 4,391,904, the disclosure of which is incorporated herein by reference. The reagent may comprise one reagent or a mixture of reagents. In a preferred embodiment of the invention, the reagent is an immunologically active substance, such as antibody, antigen, or the like, which is capable of specifically binding the analyte or competitively binding with the analyte.

The reagent component may be introduced into the permeable matrix by any appropriate method. Desireably, the method will result in the substantially uniform dispersion of the reagent throughout the filter matrix. For example, the permeable matrix may be presaturated by adding liquid reagent component to the matrix prior to insertion of the matrix into the applicator tube. Alternatively, the reagent component may be applied to the permeable matrix after the matrix is placed in the tube by inserting a narrow pipette with reagent into tip 20 and using a vacuum or capillary action to draw the reagent from the pipette into the filter matrix. A fourth alternative would be to utilize a vacuum system to draw liquid reagent into the applicator tip (as generally described in U.S. Pat. No. 4,087,248) or to utilize positive pressure to force liquid reagent into the tip (as generally described in U.S. Pat. No. 4,447,578). It is also possible to introduce solid phase reagents to the matrix material, typically by combining in a liquid slurry, by any of the techniques just described. A further method may be by inserting a hypodermic needle containing the reagent into tip 20 and injecting the reagent into the filter matrix.

The reagent component in the permeable matrix may be present in a variety of forms, including dried (by air or vacuum), lyophilized, in pellet form (preferably a plurality of discrete pellets dispersed uniformly throughout the matrix), in suspension or emulsion, in a gel, or in a stable liquid form. Liquid reagents will typically be absorbed in the matrix, while solids will be physically entrapped or absorbed within the matrix.

The present invention is useful in introducing a wide variety of reagents to virtually any type of biological sample which is liquid or which can be liquified. The reagent is reconstituted by combining with a liquid sample (or other liquid assay component) as the liquid is drawn through the permeable matrix within the applicator. The large surface area within the matrix over which the reagent is preferably dispersed allows for rapid reconstitution of reagent and thorough mixing with sample or other liquid.

The preferred method of the present invention for introducing a reagent to a liquid biological sample or other assay component comprises:

drawing at least a portion of the liquid sample or assay component from a reservoir into the applicator tube lumen through the permeable matrix, whereby the reagent is reconstituted by and mixed with the liquid sample; and discharging the combined liquid sample and reagent from the lumen of the applicator tube to an assay medium or device through the permeable matrix in a flow direction opposite to that in which the liquid sample was drawn into the applicator tube.

In a more preferred embodiment of the invention, mixing is further enhanced by introducing air in the form of bubbles into the sample/reagent solution in the lumen of the applicator tube. This action causes bubbles to percolate through the sample/reagent solution to improve mixing efficiency and reaction kinetics to allow for a more rapid reaction. This may be accomplished by drawing air through the permeable matrix behind the measured volume of sample. Air may also be introduced by placing a membrane 50 (FIG. 3) across the applicator tube 12 at a fill line, which membrane will pass air but not liquid once it is wetted. The membrane 50 will allow only the desired volume of sample to enter the applicator, but will allow addition of amounts of air to pass once the applicator tip 20 is removed from the sample. The same effect may be achieved with an impermeable barrier having one or more small orifices sized to allow the passage of air but not sample.

Therefore, the method of the present invention may further comprise introducing air in the form of bubbles into the sample/reagent solution in the applicator tube prior to discharging the sample and reagent from the applicator tube to the assay medium or device.

The applicators of the present invention containing a reagent in the permeable matrix may be used in any assay protocol which employs a step of introducing a reagent to a liquid sample or other liquid assay component. Use of the applicator of this invention allows combination of a liquid transfer step with one or more reagent addition steps, reducing the total number of steps required to perform a particular assay protocol. Moreover, reagent addition in the applicator frequently provides enhanced mixing of the reagent which can reduce the time required to perform an assay protocol and/or increase the accuracy of the assay. When used in an assay where the reagent is an immunologically active substance, the immunological binding step of the assay will typically be performed concurrently with the sample transfer step. For example, analyte may be bound with the immunological reagent as the sample is transferred from a sample reservoir medium to an assay medium or device.

Generally, the assay device will be capable of detecting, visually or otherwise, the bound analyte. For example, bound analyte will be visualized on the device, typically by reaction with enzyme-labeled antibody specific for the analyte and exposure to enzyme substrate. Enzyme-substrate systems capable of producing a colored reaction product are amply described in the patent and scientific literature. A particularly preferred assay device is described in U.S. Pat. No. 4,818,677, previously incorporated herein by reference.

The following examples are offered by way of illustration, not by way of limitation.

EXPERIMENTAL

Example 1

An applicator as illustrated in FIG. 1 was prepared having a length of 7.2 cm and an internal diameter of 0.53 cm. The filter matrix was composed of poly(ethylene terephthalate) fibers having a length of 2 cm and a diameter of about 15 $\mu$m at a density of $2.5 \times 10^5$ fibers/cm$^2$. A conventional fluid dropper bulb was provided on the upper end of the tube.

hCG positive urine was diluted with hCG negative urine to an approximate concentration of about 50 mIU/mL hCG (WHO First IRP Standard). The urine was subjected to a quantitation assay for hCG before and after being drawn and discharged from the applicator. The results are set forth in Table 1.

TABLE 1

|  | hCG Concentration |
| --- | --- |
| Prior to Filtration | 65.9 mIU/mL |
| After Filtration | 65.5 mIU/mL |
| Protein Loss | −0.6% |

Thus, the filter resulted in no substantial loss of hCG from the sample.

Example 2

The applicator from Example 1 was used to perform membrane assays in six samples of fresh morning urine free from hCG. The membrane assay was RAMP ™ hCG assays available from Monoclonal Antibodies, Inc., Mountain View, Calif. Comparative assays were run with conventional fluid droppers without a filter matrix. In both cases, the applicator or fluid dropper was used to transfer fresh sample from a collection cup to the membrane. The time necessary for the sample to be absorbed through the membrane was recorded for each sample for both the applicator and the dropper. The results are set forth in Table 2.

TABLE 2

| | Absorption Time (seconds) | | |
| --- | --- | --- | --- |
| Specimen No. | Applicator[1] | Applicator[2] | Fluid Dropper (without filter) |
| 1 | 4 | 5 | 12 |
| 2 | 2.5 | 3 | 3 |
| 3 | 3 | 8 | >60 |
| 4 | 3 | 4 | 6 |
| 5 | 2.5 | 6 | 9 |
| 6 | 3 | ND | 7 |

[1]Average of two tests, first drop discarded.
[2]First drop not discarded.
ND: Not done.

As can be seen from the above results, a substantial improvement in the flow characteristics of the urine samples are achieved with the applicator of the present invention.

Example 3

Two antibodies specific for different and nonoverlapping epitopes on the hCG antigen, each antibody conjugated to the enzyme alkaline phosphatase, were mixed together in a diluent (0.05 M Tris, 0.1 M NaCl, 0.001 M MgCl$_2$) and adjusted to pH 7.4 ("hCG conjugate").

An applicator was prepared as in Example 1, except that the filter matrix was composed of fibers having a length of 1 cm. hCG antibody conjugate solution (25 μL) prepared above was added to the filter by inserting a pipette containing the conjugate solution through the tapered tip of the applicator and applying vacuum. hCG positive urine (400 μL) was then drawn from a sample container into the applicator through the filter matrix, and the applicator was removed from the sample container, after which the bulb was released to allow air bubbles to enter the applicator through the filter matrix. The contents of the applicator were incubated in the tube for 30 sec. and were then applied to a membrane consisting of nylon between two pellon layers to which had been immobilized on the top layer an antibody specific for a third non-overlapping epitope on the hCG antigen. The contents were incubated on the membrane for 1 min. A chromogenic material which produces a blue reaction product when exposed to alkaline phosphatase ("wash/substrate"; 6 drops) was added to the pad, the reaction was incubated for 3 min., and then a solution to stop the reaction was added ("stop"; 4 drops). The results showed a distinct, well-colored blue spot on the membrane with no background.

The above procedure was repeated, except that there was no incubation of the contents in the applicator prior to discharge of the contents onto the membrane. The contents were incubated on the membrane for 10 sec. and treatment was then continued as above. The results gave a lighter blue spot and a clean background.

Example 4

To the filter of an applicator as in Example 3 was added 50 μL of a 1:1 mixture of glycerol:hCG conjugate. The loaded applicator was held at room temperature for 5 days. 250 mIU/mL hCG urine (500 μL) was then drawn up into the applicator, followed by air, and incubated for 30 sec. The contents were dispensed onto a membrane as in Example 3, incubated for 10 seconds and treated as in Example 3. A blue spot of good color intensity resulted.

Example 5

Lyophilized conjugate was prepared as follows: To assist in dissolving and for protection during freezing, a solution of 2 mg/mL protease-free BSA, 10% mannitol was mixed 1:1 with hCG conjugate of Example 3. This solution (70 μL) was added to an applicator as in Example 3, and the applicator was placed in a lyophilization jar and held at −80° C. overnight, after which it was lyophilized and stored at room temperature for 3 days.

A second applicator with filter containing glycerol:hCG conjugate mixture (70 μL) was prepared as in Example 4 and stored at room temperature for 5 days.

Approximately 500 μL of 250 mIU/mL hCG urine was drawn into each of the above two applicators, followed by air, after which the solution in the applicator was immediately discharged onto the membrane pad without an incubation period. As soon as each sample had finished absorbing into the pad, wash/substrate was added without prior incubation. The sample was then incubated for 3 min., after which the reaction was stopped.

Both the lyophilized and the glycerol-containing conjugates gave positive results, with the lyophilized conjugate producing a lighter color response.

Example 6

Following the procedure of Example 3, 25 μL of hCG conjugate was added to a filter in an applicator. Likewise, 50 μL of 1:1 glycerol:hCG conjugate was added to a filter in another applicator.

Following the shortened assay procedure described in Example 5, 250 mIU/mL hCG urine (500 μL) was added to each of the two applicators and processed. Conjugates from both applicators gave positive results.

Although the foregoing invention has been described in some detail by way of illustration and example for purposes of clarity of understanding, it will be obvious that certain changes and modifications may be practiced within the scope of the appended claims.

What is claimed is:

1. A method for transferring a liquid biological sample including an analyte in the presence of particulate contaminants from a reservoir to an assay device, said method employing an applicator tube having an internal filter matrix at one end thereof, the filter matrix is constructed so as to filter substantially all of said particulate contaminants but allow said analyte to flow therethrough, said method comprising:
   drawing at least a portion of said liquid biological sample from the reservoir into the applicator tube through said filter matrix; and
   discharging said liquid biological sample including said analyte from the applicator tube to the assay device through said filter matrix in a flow direction opposite to that in which said liquid biological sample containing particulate contaminants was drawn into the applicator tube, whereby said particulate contaminants within said liquid biological sample are entrapped by said filter matrix and separated from said discharged liquid biological sample including said analyte.

2. A method as in claim 1, wherein said liquid biological sample is selected from the group consisting of urine, serum, blood, plasma, cerebral fluid, spinal fluid, ocular lens liquid, saliva, sputum, semen, cervical mucus, liquified scrapings, and swab samples.

3. A method as in claim 1, wherein said liquid biological sample is urine.

4. A method as in claim 1, wherein said filter matrix is composed of a fiber material selected from the group consisting of polyester, cellulose acetate, and polyacrylonitrile.

5. A method as in claim 1, wherein said liquid biological sample is drawn into the applicator tube using a vacuum bulb.

6. A method as in claim 1, wherein the liquid sample is drawn into the applicator by a vacuum source on said assay device.

7. A method as in claim 1, wherein a first part of said liquid biological sample drawn into the applicator tube is disposed of prior to discharging to said assay device.

8. A method for introducing a reagent to a liquid assay component including an analyte and particulate contaminants, where the method employs an applicator tube comprising at one end thereof an internal permeable matrix having the reagent dispersed therein, the internal permeable matrix is constructed so as to filter substantially all of said particulate contaminants but allow said analyte and reagent to flow therethrough, said method comprising:
   drawing at least a portion of said liquid assay component including said analyte and particulate contaminants from a reservoir into the applicator tube through said permeable matrix, whereby said reagent is reconstituted by and mixed with said liquid assay component including said analyte; and discharging said liquid assay component including said analyte and reagent from the applicator tube to an assay medium or device through said permeable matrix in a flow direction opposite to that in which said liquid assay component including said analyte and particulate contaminants was drawn into the applicator tube whereby said particulate contaminants within said liquid assay component are entrapped by said permeable matrix and separated from said discharged liquid including said analyte and reagent.

9. A method as in claim 8, wherein said liquid assay component is a liquid sample selected from the group consisting of urine, serum, blood, plasma, cerebral fluid, spinal fluid, ocular lens liquid, saliva, sputum, semen, cervical mucus, liquified scrapings, and swab samples.

10. A method as in claim 9, wherein said liquid assay component is urine.

11. A method as in claim 8, wherein said permeable matrix is composed of a fiber material selected from the group consisting of polyester, cellulose acetate, and polyacrylonitrile.

12. A method as in claim 8, wherein said reagent is an immunologically active substance.

13. A method as in claim 12, wherein said reagent is selected from the group consisting of monoclonal or polyclonal antibody and monoclonal or polyclonal antibody conjugates.

14. A method as in claim 8, wherein said liquid assay component is drawn into the applicator tube using a vacuum bulb.

15. A method as in claim 8, wherein said liquid assay component is drawn into the applicator tube by a vacuum source on said assay device.

16. A method as in claim 8, wherein said reagent is in liquid form and absorbed within the matrix.

17. A method as in claim 8, wherein said reagent is in solid form and physically entrapped or absorbed within the matrix.

18. A method for introducing a reagent to a liquid assay component including an analyte and particulate contaminants, where the method employs an applicator tube comprising at one end thereof an internal permeable matrix having the reagent dispersed therein, the internal permeable matrix is constructed so as to filter substantially all of said particulate contaminants but allow said analyte and reagent to flow therethrough, said method comprising:

drawing at least a portion of said liquid assay component including said analyte and particulate contaminants from a reservoir into the applicator tube through said permeable matrix, whereby, said reagent is reconstituted by and mixed with said liquid assay component including said analyte;

introducing air in the form of bubbles into the applicator tube to improve reaction kinetics of reaction between said analyte and reagent; and discharging said liquid assay component including said analyte and reagent from the applicator tube to an assay medium or device through said permeable matrix in a flow direction opposite to that in which said liquid assay component containing said analyte and particulate contaminants was drawn into the applicator tube whereby said particulate contaminants within said liquid assay component are entrapped by said permeable matrix and separated from said discharged liquid including said analyte and reagent.

19. A method as in claim 18, wherein said air is introduced by drawing air through said permeable matrix after a predetermined volume of said liquid assay component has been drawn into the tube.

20. A method as in claim 18, wherein said liquid assay component is a liquid sample selected from the group consisting of urine, serum, blood, plasma, cerebral fluid, spinal fluid, ocular lens liquid, saliva, sputum, semen, cervical mucus, liquified scrapings, and swab samples.

21. A method as in claim 20, wherein said liquid assay component is urine.

22. A method as in claim 18, wherein said permeable matrix is composed of a fiber material selected from the group consisting of polyester, cellulose acetate, and polyacrylonitrile.

23. A method as in claim 18, wherein said reagent is an immunologically active substance.

24. A method as in claim 23, wherein said reagent is selected from the group consisting of monoclonal or polyclonal antibody and monoclonal or polyclonal antibody conjugates.

25. A method as in claim 18, wherein said liquid assay component is drawn into the applicator tube using a vacuum bulb.

26. A method as in claim 18, wherein said liquid assay component is drawn into the applicator by a vacuum source on said assay device.

27. A method as in claim 18, wherein said reagent is in liquid form and absorbed within the matrix.

28. A method as in claim 18, wherein said reagent is in solid form and physically entrapped or absorbed within the matrix.

* * * * *